United States Patent [19]

Lehmann et al.

[11] Patent Number: 5,046,816

[45] Date of Patent: Sep. 10, 1991

[54] DEVICE FOR ARRANGING OPTICAL FIBERS IN AN ENDOSCOPE OPTICAL SYSTEM

[75] Inventors: Helmut Lehmann, Kraichtal-Menzingen; Siegfried Karst, Eisingen, both of Fed. Rep. of Germany

[73] Assignee: Richard Wolf GmbH, Knittlingen, Fed. Rep. of Germany

[21] Appl. No.: 556,043

[22] Filed: Jul. 20, 1990

[30] Foreign Application Priority Data

Sep. 4, 1989 [DE] Fed. Rep. of Germany ....... 3929285

[51] Int. Cl.[5] ............................................. G02B 23/26
[52] U.S. Cl. ................................... 385/117; 385/115
[58] Field of Search ................ 350/96.24, 96.25, 96.26

[56] References Cited

U.S. PATENT DOCUMENTS

| 3,261,351 | 7/1966 | Wallace | 350/96.26 X |
| 3,434,775 | 3/1969 | Gosselin | 350/96.26 |
| 3,498,286 | 3/1970 | Polanyi et al. | 350/96.26 X |
| 4,173,392 | 11/1979 | Ekinaka et al. | 350/96.26 |
| 4,576,147 | 3/1986 | Hashiguchi | 350/96.26 X |
| 4,664,486 | 5/1987 | Landre et al. | 350/96.26 X |

FOREIGN PATENT DOCUMENTS 1054009  1/1967  United Kingdom ............. 350/96.26

*Primary Examiner*—John D. Lee
*Attorney, Agent, or Firm*—Panitch Schwarze Jacobs & Nadel

[57] ABSTRACT

In an endoscope optical system comprising an inner tube accommodating the optical components of the system and an outer tube enclosing the inner tube, optical fibers are disposed in the chamber defined between the two tubes, for transmitting light to a site to be inspected by means of the endoscope. For uniform illumination of the site to provide images to satisfactory quality, coaxial or paraxial arrangement of the inner tube within the outer tube is achieved by bridging the chamber by means of webs extending longitudinally of the tubes, the optical fibers being accommodated in sub-chambers defined between the webs.

7 Claims, 1 Drawing Sheet

DEVICE FOR ARRANGING OPTICAL FIBERS IN AN ENDOSCOPE OPTICAL SYSTEM

FIELD OF THE INVENTION

The invention relates to an endoscope optical system comprising a inner tube accommodating optical components of said system, an outer tube enclosing said inner tube to define a chamber and optical fibres disposed in said chamber.

The optical fibers transmit light to a site to be inspected by means of the endoscope.

BACKGROUND OF THE INVENTION

For achieving uniform illumination of the image field and a high quality image, in an endoscope, the optical fibers must be arranged as far as possible concentrically about the inner tube. In the manufacture of endoscope optical systems, therefore, the optical fibers are distributed uniformly about the inner tube and are fastened to the inner tube, for example, by means of a thread. The inner tube is then inserted into the outer tube. Since no special-purpose device is available for centering the tubes, it may occur during the insertion of the inner tube into the outer tube, that the optical fibers are pushed out of their position on the periphery of the inner tube, so that the inner and the outer tubes become eccentrically located relative to one another and sections of the inner tube no longer extend parallel to the centre line of the outer tube. The resulting uneven distribution of the optical fibres at the distal end of the optical system produces defective, that is to say patchy, illumination of the image field and, because sections of the inner tube accommodating the optical components are not parallel to the outer tube, the image is of unsatisfactory quality. This centering problem is particularly acute in the manufacture of long and thin optical systems having a 0° line of sight.

There is disclosed in DE-A-23 61 873 an apparatus for arranging a plurality of small-diameter optical fiber concentrically about a single large-diameter optical fiber. The large-diameter optical fiber is passed through a central guide sleeve of a wooden guide plate and the small-diameter optical fibers are passed through a plurality of guide sleeves disposed in the guide plate in one or more concentric circles about the central guide sleeve. Although this procedure allows of exact positioning of the optical fibers on the inner tube in the manufacture of endoscope optical systems, the problem of centering the unit so produced in the outer tube upon its insertion thereinto, is not avoided.

SUMMARY OF THE INVENTION

It is an object of the present invention to achieve coaxial or precisely paraxial arrangement of the inner and outer tubes and uniform distribution of the optical fibers in the chamber defined therebetween.

According to the present invention, therefore, said chamber is bridged by longitudinally extending webs and is subdivided into sub-chambers which accommodate the optical fibers. The webs may be formed by wires made, for example, of a suitable metal or of a light-conducting material. The webs and the inner tube may be manufactured as a single unit.

By virtue of the invention there is achieved precise mutual alignment of inner and outer tubes and the sub-chambers defined between the webs enable even disposition of the fibers providing uniform illumination of the image field of, and high-quality of the image of, the endoscope.

In order to prevent dislocation of the webs and the optical fibers during the insertion of the inner tube into the outer tube, the webs and the optical fibers may be fixed to the inner tube at least in the region of the distal end of the optical system, or alternatively behind said distal end, by adhesion or by tying them up by means of thread.

DETAILED DESCRIPTION OF THE INVENTION

Figure 1:
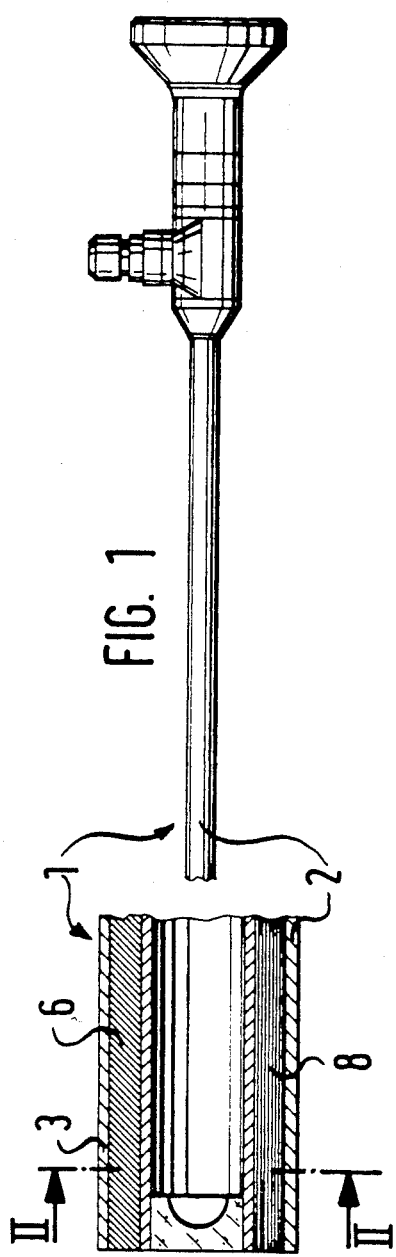
FIG. 1 is a side view of an endoscope having an endoscope shaft, and an enlarged longitudinal sectional view of said shaft showing an optical system of the endoscope.
Figure 2:
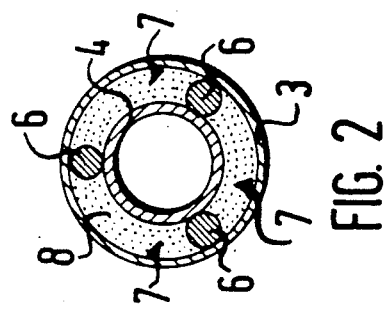
FIG. 2 is a cross-sectional view taken on the lines II—II of FIG. 1.

As shown in FIGS. 1 and 2, an endoscope optical system 1 having a 0° line of sight, comprises an outer tube 3 providing the shaft 2 of the endoscope and an inner tube 4 accommodating optical lenses. The outer tube 3 and the inner tube 4 cooperate to define an annular chamber. For centering the tubes 3 and 4 relative to each other, there are provided webs 6, which are three in number in the present example, and which bridge said annular chamber between the tubes 3 and 4 to define sub-chambers 7 therebetween. The sub-chambers 7 accommodate optical fibers 8 which are sufficient in number to fill the sub-chambers 7.

Figure 3:
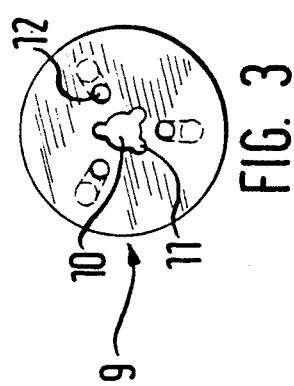
FIG. 3 is an elevational view of a disc device for aiding the assembly of said optical system.
Figure 4:
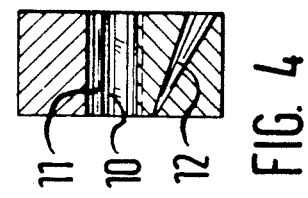
FIG. 4 is an axial sectional view of said disc device.

In order to insert the webs 6 and the fibers 8 into the tube 3, there is provided an assembly aid disc device 9 (FIGS. 3 and 4). For use in the assembly of an optical system having a cross section as shown in FIG. 2, the device 9 has a central bore 10 for accommodating the inner tube 4, into which bore 10 open three bores 11 paraxial therewith. Further, conical, bores 12 in the device 9, disposed at a uniform radial distance from the central bore 10, extend obliquely towards the axis thereof.

In use of the device 9, the inner tube 4 is inserted into the central bore 10 of the device 9, the webs 6 which are in the form of wires, being then passed through the bores 11 and fixed to the tube 4 by means of solder or an adhesive. The fibers 8 are then pushed through the bores 12 and inserted between adjacent webs 6. The fibers 8 are then tied, by means for example of a thread, or are glued together with the web 6 at least in the distal region of the tube 4. The inner tube 4 is then inserted into the outer tube 3, the webs 6 and the optical fibers 8 guided through the respective bores 11 and 12 of the disc device 9 being brought to their intended required positions on the inner tube 4.

Webs 6 in the form of wires and the fibers 8 may also be fixed in their required positions either by tying them securely, for example, by means of a thread or by sticking them together by means of an adhesive, behind the distal end of the inner tube 4. Space is thereby left free which would otherwise be taken up by the adhesive or solder used to fasten the webs 6 to the tube 4, thus allowing more fibers 8 to be accommodated between an adjacent pair of webs 6.

Figure 5:
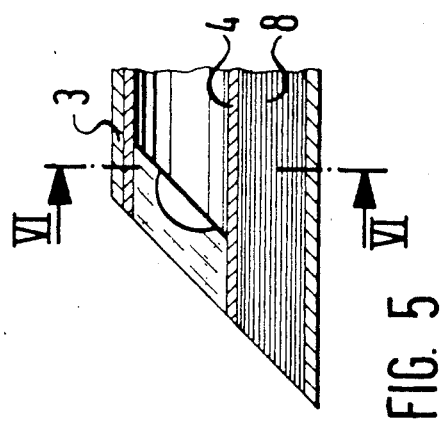
FIG. 5 is a partial longitudinal sectional view through the endoscope shaft of a side-look endoscope, showing the optical system thereof.
Figure 6:
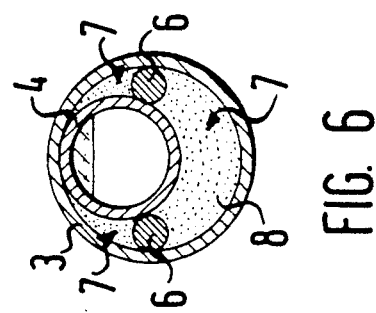
FIG. 6 is a cross sectional view taken on the lines VI—VI of FIG. 5.

Especially in the manufacture of an optical system having a line of sight which differs from 0° (FIGS. 5 and 6), there may be only one or two webs 6, the inner tube 4, being coaxial with, or non-coaxial and paraxial with the outer tube 3, the assembly aid device being advantageously modified accordingly.

The webs 6 may be made of a metal, for example MONEL metal having good sliding properties and the cross-sections of the webs 6 may be of any suitable configuration. The webs 6 may be made of a light conducting material so that they do not occasion loss of light. The inner tube may be provided with longitudinally extending webs during its manufacture, the webs thereby being formed integrally with the inner tube.

What is claimed is:

1. An endoscope optical system, comprising:
   an inner tube accommodating optical components of said system;
   an outer tube enclosing the inner tube whereby said tubes define a chamber therebetween;
   optical fibers disposed between said tubes; and
   separately formed wires extending longitudinally of said tubes and bridging said chamber thereby to subdivide it into subchambers, said fibers being accommodated in said subchambers.

2. An optical system as claimed in claim 1, wherein said wires are made of a light conducting material.

3. An optical system as claimed in claim 1, wherein the wires and said fibers are fixed to the inner tube by adhesion at least in the region of the distal end thereof.

4. An optical system as claimed in claim 1, wherein the wires and the optical fibers are fixed to the inner tube by means of thread at least in the distal end region thereof.

5. An optical system as claimed in claim 1, wherein the wires and the optical fibers are fixed by means of thread behind the distal end of the inner tube.

6. An optical system as claimed in claim 1, wherein the wires and the optical fibers are fixed by adhesion behind the distal end of the inner tube.

7. An optical system as claimed in claim 1 wherein said wires are circular in cross-section.

* * * * *